United States Patent [19]

Glassner et al.

[11] Patent Number: 5,143,834
[45] Date of Patent: Sep. 1, 1992

[54] PROCESS FOR THE PRODUCTION AND PURIFICATION OF SUCCINIC ACID

[76] Inventors: David A. Glassner, 4454 Satinwood Rd., Okemos, Mich. 48864; Rathin Datta, 442 W. Melrose Ave., #3, Chicago, Ill. 60657

[21] Appl. No.: 325,404

[22] Filed: Mar. 17, 1989

Related U.S. Application Data

[63] Continuation-in-part of Ser. No. 301,788, Jan. 25, 1989, which is a continuation-in-part of Ser. No. 873,031, Jun. 11, 1986, abandoned.

[51] Int. Cl.$^5$ .......................... C12P 7/46; C12P 1/04; C12N 1/20; C07C 51/42
[52] U.S. Cl. ................................ 435/145; 435/252.1; 435/170; 435/822; 562/593; 562/590; 204/182.3; 204/182.4
[58] Field of Search ................... 204/182.4, 182.3, 186; 562/593, 590; 435/144, 145, 170, 822, 252.1

[56] References Cited

U.S. PATENT DOCUMENTS

| | | | |
|---|---|---|---|
| 4,110,175 | 8/1978 | Ahlgren et al. | 204/180 P |
| 4,678,553 | 7/1987 | Mandle et al. | 204/182.6 |
| 4,766,161 | 8/1988 | Chlanda et al. | 521/27 |

FOREIGN PATENT DOCUMENTS 8318631  5/1985  France .

OTHER PUBLICATIONS

Hopgood et al., Aust. J. Biol. Sci., vol. 20, pp. 165–192 (1967).
Caldwell et al., J. Bacteriol., vol. 98, pp. 668–676 (1969).
Caspari et al., Arch Microbiol., vol. 135, pp. 16–24 (1983).
Davis et al., Int. J. Syst. Bacteriol., vol. 26, pp. 498–504 (1976).
"AQUATECH" System, Product Brochure, Allied Signal Corporation, 1985.
Hongo, J., Nomura. Y. and M. Iwahara, "Novel Method of Lactic Acid Production by Electrodialysis Fermentation," Appl. Environ. Microbiol. 52, 2, 314–319, Aug., 1986.
Nomura, Y., Iwahara, M. and M. Hongo, "Lactic Acid Production by Electrodialysis Fermentation Using Immobilized Growing Cells." Biotechnol. & Bioeng. 30, 788–793, Oct. 1987.
Boyer, R. F. "Modern Experimental Biochemistry", 1986.
The Merck Index, 1983, 10th ed, p. 234.
Gerhardt et al., Manual of Methods for General Bacteriology, ASM, 1981, pp. 67–69.
Bergey's Manual of Systematic Bacteriology Krieg et al., ed, 1984, Williams Wilkins, pp. 604–605.

*Primary Examiner*—Irene Marx
*Attorney, Agent, or Firm*—Quarles & Brady

[57] ABSTRACT

A process for producing and purifying succinic acid comprises growing a succinate salt-producing microorganism on an inexpensive substrate containing carbohydrate, other nutrients, sodium ions and tryptophan under a $CO_2$ partial pressure until most of the carbohydrate is converted to succinate. The fermentation broth is then electrodialyzed to recover and concentrate the succinate salt in an aqueous stream which is subjected to water-splitting electrodialysis to form base and a succinic acid product. The resulting succinc acid product is treated first with a strongly acidic ion exchanger in the acid form to remove any sodium or other cations and then treated with a weakly basic ion exchanger in the free base form to remove any sulfate ions or sulfuric acid and to obtain a highly purified succinic acid product.

4 Claims, 3 Drawing Sheets

PROCESS FOR THE PRODUCTION AND PURIFICATION OF SUCCINIC ACID

RELATED CASE

This application is a continuation-in-part of an earlier copending application U.S. Ser. No. 07/301,788, filed Jan. 25, 1989, which is a continuation-in-part of U.S. Pat. Ser. No. 873,031, filed Jun. 11, 1986, now abandoned.

FIELD OF THE INVENTION

The present invention relates to an improved process for the production and purification of succinic acid by anaerobic fermentation, electrodialysis and ion exchange.

BACKGROUND OF THE INVENTION

Succinic acid and its derivatives are widely used as specialty chemicals for applications in polymers, foods, pharmaceuticals, and cosmetics. Furthermore, succinic acid is a valuable 4-carbon intermediate useful for the production of 1,4-butanediol, tetrahydrofuran, and gammabutyrolactone.

Although the succinate ion is a common intermediate in the metabolic pathway of several anaerobic microorganisms, there are no examples of any prior art fermentation that produces succinate in large amounts or with high yields. For example, succinate is a key intermediate for anaerobic fermentations by propionate-producing bacteria, but it is only produced in low yields and in low concentrations.

Succinate is also produced by anaerobic rumen bacteria. These bacteria include *Bacteroides ruminicola* (hereafter written *B. rumincola*) whose growth and metabolism is described by Howlett, et al., *Applied Environ. Microbiol.*, 32, 274–283 (1976) and *Bacteroides amylophilus* (hereafter written *B. amylophilus*) whose culture and growth are described by Caldwell, et al., *J. Bacteriol.*, 98, 668–676 (1969) and by Hamlin, et al., *J. Bacteriol.*, 72, 548–554 (1956).

Although the rumen bacteria give higher yields of succinate than do the propionate-producing bacteria, the reported fermentations were run in very dilute solutions and gave a variety of products in generally low yields. Moreover, the rumen organisms tend to lyse after a comparatively short fermentation time, thereby, leading to unstable fermentations.

In 1961, Anderson and Ordal isolated a facultative anaerobe, *Cytophaga succinicans*, which produced succinate, acetate, and formate from dextrose with fixation of carbon dioxide, *J. Bact.*, 81, 139 (1961). However, this organism produced succinate in such low concentrations that it would not be economically feasible to recover succinic acid from the fermentation medium. Similar results were observed with the *Bacteroides fragilis* obtained from the gastrointestinal tract, Caspari, et al., *Arch. Microbiol.*, 135, 16–24 (1983).

In order to develop a commercially attractive process to produce succinic acid by fermentation, several important fermentation and product purification criteria need to be accomplished. The fermentation should be high yield (wt%) and produce a high product concentration using inexpensive raw materials and nutrients. Since anaerobic fermentations are run at neutral or near neutral pHs, salts of organic acids rather than the acids themselves are produced. The fermentation broth also contains cells, protein and other undesirable materials.

The desired product from the process is the purified acid which can be used for specialty or commodity chemical manufacture. Hence, a high yield, economical fermentation process has to be integrated with an efficient recovery and purification process.

Electrodialysis (ED) is a well known separation process where ionized compounds are separated from non-ionized or weakly ionized compounds in aqueous solutions based on transport through ion exchange membranes in an electric field. The process has been used in a commercial scale in the chlor-alkali, desalination, metal-processing, wastewater treatment, pharmaceutical and food processing industries. Since in a fermentation broth the succinate salt is ionized, whereas the carbohydrates and proteins and amino acids are either non-ionized or weakly ionized, recovery and purification of succinate salt from the fermentation broth by electrodialysis is feasible.

Recently, several papers and patent applications have been published on recovery and purification of lactate from fermentation broths by conventional electrodialysis. However, in these examples, broth was either thoroughly cleaned to remove cells and proteins prior to electrodialysis or when broth containing cells was used the membrane fouled and led to a loss of efficiency. Prigent (6) disclosed a method for production of lactate from fermenting whey where the broth was filtered by ultrafiltration to remove the cells and then electrodialyzed. Hongo, Nomura and Iwahara (7) used a whole broth of *Lactobacillus delbrueckii* IFO 3534 in their electrolysis cum electrodialysis apparatus, but discovered that the efficiency was poor due to membrane fouling. These workers (8) then devised a complicated fermentation process where the cells were immobilized in alginate beads and the cell free broth was fed to the electrodialyzer. Bacterial cells are very small and to remove cells by high speed centrifugation and/or ultrafiltration is expensive both in process capital and power requirements. Cell immobilization in alginate beads is also very expensive.

It is conceivable that conventional electrodialysis, as described previously, if selective can be used to recover and concentrate succinate salt from a cell-free fermentation broth. For most specialty and commodity chemical uses of succinic acid, the acid form is required. Recent development of high efficiency bipolar membranes (9,10,11,12) for use in water-splitting electrodialysis membrane stacks, make it feasible to produce acid and base from a salt. Thus, we theorized that the desirable succinic acid and the corresponding base might be produced from the succinate salt. The base could then be recycled to the fermentation process.

The succinic acid product, after water-splitting ED, will have cationic, anionic and amino acid impurities. Ion exchange resins are capable of removing ionically charged species from solutions. Since some of the impurities in the succinic acid are ionically charged, careful selection of ion exchangers might allow removal of the impurities without removing the succinic acid itself. Cation exchangers will remove positively charged ions having a specific ionic strength. Anion exchangers will remove negatively charged ions having a specific ionic strength. Therefore, we theorized that proper selection of the types of ion exchangers, order of use, and the operating parameters may allow the removal of the succinic acid stream impurities.

For a succinic acid fermentation process to be economically attractive to produce specialty and commodity chemicals, development of a low cost fermentation and purification process is necessary. The fermentation should use low cost substrates and nutrients, the rate of fermentation should be high (high productivity), and the product concentration in the fermentation broth should be high. In addition, proper integration of an efficient and economical purification process with the fermentation is necessary.

BRIEF SUMMARY OF THE INVENTION

It is the primary object of the present invention to disclose an improved, economically attractive, succinic acid production and purification process.

We have now discovered an improved process for the production of succinic acid which includes a fermentation process which uses a robust strain of an anaerobic, succinate-producing microorganism which produces succinate salt in high concentration from a low cost fermentation medium and a purification system which uses conventional electrodialysis to recover and concentrate the succinate from a whole broth containing cells and nitrogenous impurities; a water-splitting electrodialysis to convert the succinate obtained to succinic acid and base; and, treatment with ion exchangers to remove charged impurities from the succinic acid.

As a result of our discovery, we are able to produce a succinic acid product containing less that 1% nitrogenous material (protein) and less than 10 ppm of contaminating sulfate ions. The product also may contain up to 20% acetic acid.

To achieve the production of low cost succinic acid, a careful integration of the fermentation process with the efficient, low cost purification process must be accomplished. In addition, the correct sequence of recovery and purification steps, along with the correct operating parameters, must be employed. Without the correct sequence of electrodialysis processes and ion exchange processes, at the operating conditions specified, the production of a low cost succinic acid product of the desired purity is not feasible.

DESCRIPTION OF PREFERRED EMBODIMENT

Figure 1:
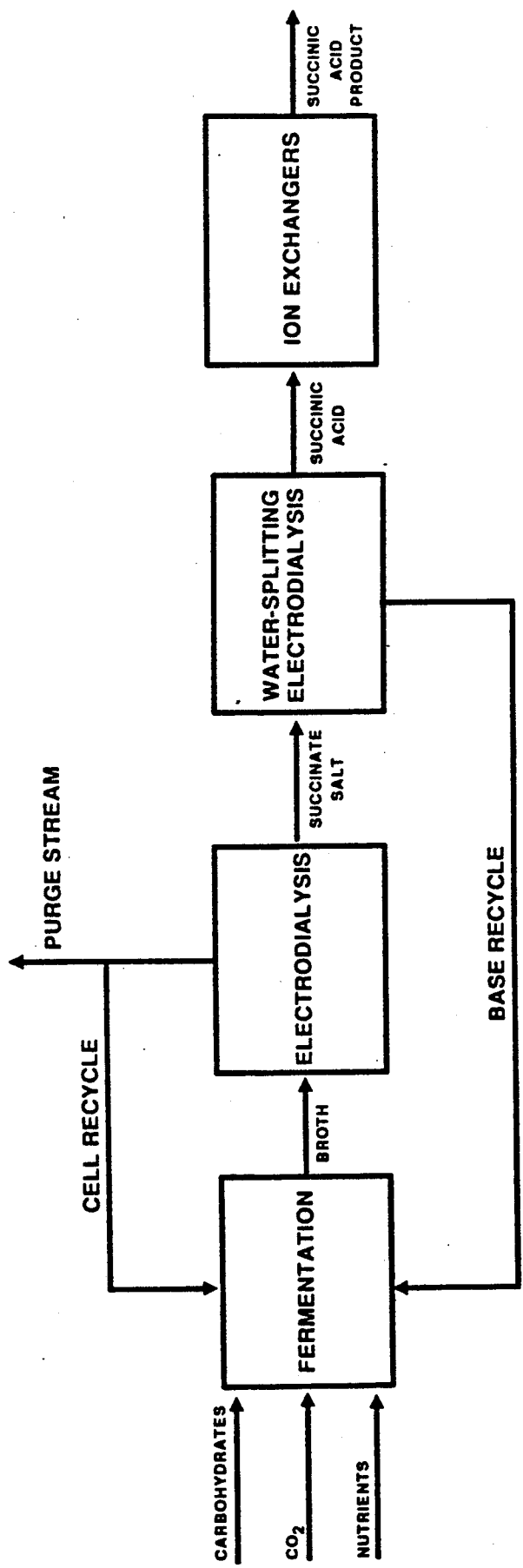
FIG. 1 is a flow sheet showing the process of the present invention.

In the preferred practice of the present invention, a substantially pure culture of *A. succiniciproducens* (ATCC 53488) is anaerobically grown at a controlled pH between about 5.8 to about 6.6 in a fermentor on a medium containing carbohydrates; other nutrients, such as corn steep liquor; tryptophan; and, sodium ions under a partial pressure of at least about 0.1 atmosphere $CO_2$ until a yield of about 75 weight percent of succinate salt based on the weight of the carbohydrate is obtained and the fermentation broth contains at least about 20 g/l of succinate.

The carbohydrate used in the practice of this invention can be any carbohydrate that is fermented by the strain of bacterium used. For *A. succiniciproducens*, these carbohydrate sources include dextrose, sucrose, fructose, lactose, soluble starches, and corn syrups. The fermentation is conducted in an aqueous medium containing tryptophan, sodium ions and dissolved carbon dioxide. Other nutrients and growth factors needed for the growth and the reproduction of the microorganism employed also are added to the medium.

The concentration of carbohydrate in the medium is between about 20 g/l to about 100 g/l, preferably between about 40 g/l and about 80 g/l. Carbohydrate concentrations above about 100 g/l give solutions with such high osmotic pressures that the organisms do not grow well. Although the organisms will grow in solutions containing less than 20 g carbohydrate per liter, the concentration of product is so low that its recovery usually is not practical.

Carbon dioxide can be supplied to the fermentation medium in various ways. The medium can be sparged with $CO_2$ gas. The fermentation can be run in a pressurized reactor which contains carbon dioxide at superatmospheric pressure. The $CO_2$ can be mixed with other gases as long as the gases employed do not interfere with the growth and metabolism of the organism employed. Carbon dioxide can also be supplied to the fermentation medium by the addition of carbonates or bicarbonates which generate this gas under the conditions of the fermentation. The medium should contain dissolved $CO_2$ in equilibrium with a minimum of about 0.1 atmosphere partial pressure of carbon dioxide. In the preferred embodiment, the medium is saturated with carbon dioxide and the atmosphere contains about 0.3 atmosphere partial pressure of carbon dioxide or higher.

In order to obtain good production of succinate salt, the pH of the medium is maintained in the range of from about 5.8 to about 6.6. At higher pH values, the main product is lactate rather than succinate, while at lower pH values, the fermentation is inhibited. The pH is conveniently maintained by the addition of alkaline carbonates, alkaline earth hydroxides, or mixtures thereof.

The fermentation process of this invention is carried out at a temperature between about 20° C. and about 49° C. Optimum growth of the *A. succiniciproducens* organism is about 39° C. Since this is a strict anaerobe, fermentations using the organism are carried out under anaerobic conditions in a medium which has been sterilized by heat or other means well known in the fermentation art.

The succinate salt-containing whole broth, including cells, is transported from the fermentor and subjected to electrodialysis to recover and concentrate the succinate salt in an aqueous stream. The viable cells are recycled back to the fermentor. The succinate salt-containing aqueous stream is subjected to water-splitting electrodialysis to form an aqueous succinic acid solution and a base which can be recycled to the fermentor. The aqueous succinic acid solution is then subjected to an ion exchange polish purification with first a cationic exchanger and then an anionic exchanger to remove positively charged and negatively charged impurities and to yield a highly purified form of succinic acid. The final product preferably will contain about 70 to about 95% succinic acid, up to 30%, usually between about 5% to about 20% of acetic acid, less then 1% nitrogenous impurities and less then 10 ppm of sulfate ions or other contaminating ions.

Representatives of the microorganisms which can be used in the process are strains of *Anaerobiospirillum succiniciproducens, B. amylophilus,* and *B. ruminicola.*

The preferred microorganism, *A. succiniciproducens* (ATCC 53488), has been demonstrated to grow well on media containing carbohydrates, preferably dextrose; other nutrients, including corn steep liquor; sodium ions; and at least about 10 ppm tryptophan in the presence of a partial pressure of at least 0.1 atmosphere of $CO_2$ at a temperature of about 39° C. This strain is capable of producing high concentrations of succinate (35-50 g/l) with a high productivity (1.5 to 2.0 g/l hr). It also can produce a high concentration of succinate salt relative to cell population so that electrodialysis using special ion exchange membranes can be successfully used on whole cell-containing broth, as well as cell-free clarified broth, to purify and concentrate the succinate salt into a purified salt product. The performance of the separation process on whole broth is identical to that on clarified broth. Surprisingly, the cells in the whole broth do not foul the electrodialysis membranes. This allows the cell-containing broths to be sent directly to the electrodialysis system without pretreatment such as filtration or centrifugation.

The electrodialysis of succinate and acetate from the fermentation broth also has led to the unexpected discovery that though both succinate and acetate are recovered, the succinate is preferentially recovered. This discovery makes the very specific electrodialysis recovery even more selective. A possible explanation may have to do with the divalent nature of the succinate compared to the monovalent acetate, but the preferential transport was not expected and has not been described elsewhere.

Previous practitioners (6,7,8) have not recommended contacting electrodialysis membranes with cell-containing whole fermentation broth. They have used ultrafiltration, microfiltration, centrifugation or complex cell immobilization methods to keep cells from contacting the ED membranes. However, the results using the preferred microorganisms and preferred electrodialysis system indicate that the direct processing of whole broth prior to cell removal is feasible. This allows product to be removed from a fermentor continuously with no product loss.

Following the purification and recovery of the succinate salt by electrodialysis, the removal of the sodium ions or other suitable cations can be accomplished using water-splitting electrodialysis (9, 10, 11, 12). Energy efficient bipolar membranes (Aquatech-Allied Signal) are used to remove most of the salt cation yielding a pure acid stream and a base stream for recycle to the fermentor.

The pure acid stream contains sodium cation and sulfate and other anions which can be readily removed from the process stream using polish ion exchange columns. Treatment of the acid stream first with strongly acidic ion exchanger and then with a weakly basic ion exchanger (Dowex 50Wx8 and Rohm and Haas IRA-94, respectively) are used to remove sodium and other cations, and then sulfate and other anions, respectively. This processing also removes some residual contaminating amino acids. The resulting product is a purified succinic/acetic acid mixture suitable for use to produce specialty and commodity chemicals.

A schematic process flow diagram for succinic acid production and purification is shown in FIG. 1. The first step is the high yield, high productivity fermentation. Carbohydrates, nutrients and carbon dioxide are converted to succinate and acetate salts in the fermentor. The whole broth is then fed to the conventional electrodialyzer. From the electrodialyzer a succinate salt depleted, cell containing broth is recycled to the fermentor or purged from the system. The purified and concentrated (3 to 4 fold) succinate salts from the conventional electrodialysis unit are fed, directly or preferably after concentration by evaporation or other membrane based processes, to the watersplitting electrodialyzer. The water-splitting electrodialysis unit produces a nearly cation free succinic acid stream and a base, such as sodium hydroxide or ammonium hydroxide, for recycle to the fermentor. The succinic acid stream containing residual cations, and sulfate and other anions, is sent through two ion exchange polishing columns. The first treatment with a strongly acidic ion exchanger, in the acid form, removes sodium and other cations and the subsequent treatment with a weakly basic ion exchanger, in the free base form, removes sulfuric acid and sulfate impurities without removing succinic acid from the stream. A succinic acid and acetic acid product with a nitrogenous impurities content lower than 1% (dry basis) and less then 10 ppm sulfate or other contaminating ions is the product from the process. Thus an efficient and economical process for production and purification of succinic acid is obtained.

Some further process variations may include:

(1) Microfiltration or ultrafiltration for cell and proteinaceous material recycle prior to conventional electrodialysis.

(2) Crystallization of the final product st remove succinic acid from the acetic acid and all impurities to produce 100% pure succinic acid.

To achieve the production of low cost succinic acid a careful integration of the fermentation with an efficient, low cost recovery process has to be accomplished. The correct sequence of recovery and purification steps along with the correct operating parameters are needed. Treatment with first a carefully selected strongly acidic cation exchanger and then with a proper weakly basic anion exchanger are required for the polish purification. Without the demonstrated sequence of electrodialysis processes and ion exchange processes and the operating conditions specified, the production of low cost succinic acid from carbohydrate does not appear to be feasible.

Novel features of the process of the present invention (i) high yield and high productivity fermentation with low cost raw materials;

(ii) economical electrodialysis purification from whole fermentation broth without fouling due to whole cells;

(iii) preferential recovery of the desired succinate salt over the by-product acetate salt through these membranes under the process conditions developed;

(iv) efficient conversion of the succinate salt to succinic acid and base using water-splitting electrodialysis;

(v) a purification of the succinic acid by ion exchange resins to produce a highly purified succinic acid product.

Figure 2:
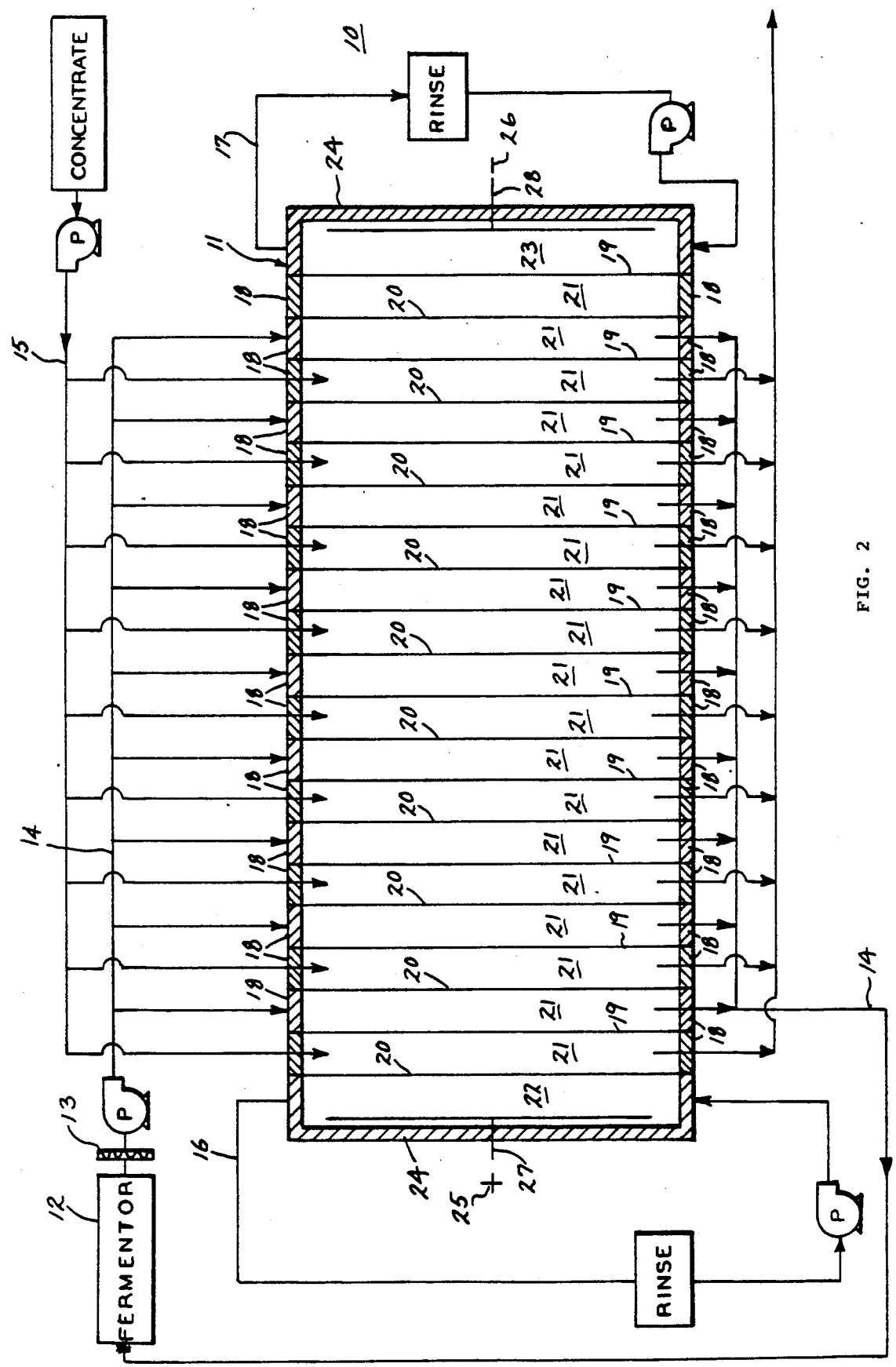
FIG. 2 is a schematic illustration of the preferred electrodialysis system; and, FIG. 3 is a graph showing the effect of tryptophan on the fermentation rate.

In FIG. 2 of the drawing, an electrodialysis apparatus 10 is shown which includes a cell stack 11, a fermentor 12, a screen 13, a feed solution injection, a recirculation and removal system 14, a concentrate recirculation and removal system 15, an anolyte rinse system 16 and a catholyte rinse system 17.

It will be appreciated that the apparatus illustrated in the drawing is for purposes of illustration and that modifications thereof can be made by those skilled in the art without departing from the scope of the present invention.

Cell stack 11 may be any known type of membrane assembly such as a plate and frame assembly wherein a plurality of suitably perforated flow distribution gaskets support and seal the peripheries of a plurality of anion-permeable membranes 19 and cation-permeable membranes 20 in parallel spaced relation to form a series of parallel cells and end cells 22 and 23. Each cell 21 is defined by a pair of membranes 19 and 20 and a gasket 18. The end cells and 23 are respectively defined by a membrane 19 and a membrane 20 and end caps 24. Disposed within end cell 22 is a suitable anode 25 and a cathode 26 is disposed in the opposite end cell 23. Anode 25 and cathode 26 are connected respectively to the positive and negative terminals of a suitable power source (not shown) through leads 27 and 28. Cell stack 11 also includes suitable couplings (not shown) for admitting and removing liquids from each of cells 21. The components of the cell stack 11 can be held in an abutting relation by suitable clamps or tie rods (not shown).

The membranes 19 are anion-permeable and cationimpermeable and the membranes 20 are cation-permeable and anion-impermeable membranes. Suitable materials for use as membranes 19 and 20 include anion and cation exchange resins having active ion capture sites, respectively. The preferred membranes 19 are fabric reinforced microheterogeneous interpolymer membranes, such as the anion exchange membranes manufactured by Asahi Glass Co. SELEMION AMV membranes, while the preferred membranes 20 are the SELEMION type CMR cation exchange membranes available from the same source. The membranes are described in U.S. Pat. No. 4,678,553 and others. Properties for these two membranes are set forth in Table I.

As seen in FIG. 1, the succinate salt enriched solution, also called the concentrate, is transmitted to a water-splitting electrodialysis apparatus to convert the succinate salt to succinic acid. The feed solution, minus the succinate salt, but including the viable cells is recirculated back to the fermentor. While the electrodialysis is going on the electrodes are rinsed with a suitable electrolyte solution, such as $Na_2SO_4$ or succinate salt in water, circulated by the rinse systems 16 and 17. The process can be operated on either a batch or continuous basis.

The present invention is further described and illustrated by the following experimental work:

Fermentations

The anaerobic fermentation test runs were conducted in 2 l New Brunswick Multigen benchtop fermentors. The initial broth volume was 1.0 liters. Media components, unless otherwise stated, are listed below:
 50 g/l Dextrose
 10 g/l Corn Steep Liquor (Dry Basis)
The media solution was placed in the fermentor and autoclaved. After removal from the autoclave, the fermentor was sparged with $CO_2$ gas and 10 ml of 3M sodium carbonate or 3.5 g/l of sodium chloride to add sodium ions, 25 ppm tryptophan, and 125 ppm of cysteine HCl/sodium sulfide were added to the fermentor. The $CO_2$ flow was stopped by clamping the outlet hose. The media and fermentor were allowed to reduce for one hour. The fermentor was then ready for inoculation using a 5% v/v inoculum. In all experiments carbon dioxide was sparged at a 10 cm3/min rate, unless otherwise noted.

Feed materials, for electrodialysis recovery of sodium succinate were produced using an 80 l fermentor in the pilot plant.

The anaerobic fermentation was performed at 39° C. in a fermentor with an initial volume of 55 l for 29 hours. The fermentor used was a 80 l New Brunswick Scientific Pilot Plant Fermentor. The media contained approximately 35 g/l dextrose, 10 g/l corn steep liquor, 3.5 g/l of NaCl and 25 ppm tryptophan. A 5% inoculum was used. The pH was maintained between

TABLE 1

| TYPES AND PROPERTIES OF SELEMION MEMBRANES | | | |
|---|---|---|---|
| DESIGNATION | CMR | AMV | REMARKS |
| Type | Strongly acidic cation-permeable membrane ($Na^+$ type) | Strongly basic anion-permeable membrane ($Cl^-$ type) | |
| Transport number  T $Na^+$ | Over 0.92 | — | Calculated from the membrane potential: 0.5/1.0 mol/P NaCl solution at 25° C. |
| T $Cl^-$ | — | Over 0.94 | |
| T$Ca^{++}$ + $Mg^{++}$ | Under 0.04* | — | Measured by electrodialysis of sea water at 2A/dm$^2$ |
| Resistance per unit area X-cm$^2$ | 2.0–2.3 | 2.0–3.0 | Measured by 1000 Hz-AC 0.5 mol/P NaCl at 25° C. |
| Thickness mm | 0.13–0.15 | 0.12–0.15 | |
| Bursting strength kg/cm$^2$ | 3–4 | 3–5 | |
| Use | General desalination/concentration Sea water concentration | General desalination/concentration | |

*After treatment

In the preferred practice of the invention, the whole broth is pumped from the fermentor 12 through the screen 13 which removes larger than cell size particles. The whole broth, minus those particles, is transported via system 14 to the cells 21 where it is subjected to an electrical current which causes the succinate ions to migrate through the permeable membrane 19 into a concentrated succinate salt solution which is circulating in the system 15 on the other side of the membrane 19.

6.1-6.3 by addition of sodium carbonate on a demand basis. Agitation speed was 100 rpm.

The cells in the fermentation broth, when indicated, were removed by processing the broth through a AMICON DC-30 ultrafiltration unit with a hollow fiber cartridge of 0.2 micron pore size.

Freshly prepared whole broth (containing viable cells) from the same fermentation was used for the whole broth experiments. The whole broth was screened through a 200 mesh wire screen to remove large particles before being charged to the electrodialysis system.

The product of the fermentation was then purified by first running it through a conventional electrodialysis unit equipped with membranes which were selective for anions and cations.

The electrodialysis stack consists of an alternating series of anion and cation selective membranes separated by flow distribution gaskets. The membranes are bound on one end by an anolyte compartment and an anode while on the other end by a catholyte compartment and cathode. See FIG. 2 for illustration. The stack pack for evaluation was provided by HPD Inc., (Naperville, Ill.) and contained membranes manufactured by Asahi Glass Co. (Japan). The stack pack contained the following:

10 cell pairs
anion membrane - AMV
cation membrane - CMR
effective area - 178 $cm^2$
electrolyte - 1M Sodium Succinate in Water The unit consists of three independent flow channels fed to the electrodialyzer stack pack. The three streams are:

(1) diluting stream—feed materials, broth
(2) concentrating stream—product
(3) electrolyte—sodium succinate or sodium sulfate From each reservoir, material was pumped through a valve, rotameter, pressure gauge, the stack pack, and then back to the reservoir. Another set of five gallon containers was located below each reservoir for removal purposes.

The electrical current was supplied by a Hewlett Packard (HP) regulated DC power supply model 6268B. It was connected to the anode and cathode of the membrane stack and could produce 0-20 amperes and deliver 0-50 volts. A Fluke A75 multimeter was used to measure the voltage drop across the membranes (excluding electrodes). Two platinum wires were inserted between eight cell pairs of membranes and then connected to the voltmeter.

An Aquatech-Allied Signal (Warren, NJ) two compartment bipolar membrane stack was used for processing organic salts into organic acids and their corresponding base. The stack designed for this process consisted of alternating cation permeable and bipolar membranes. Anode and cathode compartments are bound by a nafion membrane at each end of the membrane stack. The membrane stack contained the following:

8 cell pairs
-cation membrane
-bipolar membrane
effective area 102. 4$cm^2$
electrolyte (2.5N NaOH)

The unit consists of three independent flow channels fed to the electrodialyzer stack. The three streams are:

1. Acid stream (initially the sodium succinate salt stream)
2. Base stream (becomes more concentrated as run proceeds)
3. Electrode rinse stream (2.5N NaOH)

Before making actual runs, permissible current density (PCD) was determined to obtain a safe range for operating current density. For these runs, only two reservoirs were used. One reservoir supplied broth to both the diluting and concentrating compartments and then was pumped back to the reservoir. The second reservoir was for the electrolyte.

The unit was operated at low current and the voltage was recorded every 30 seconds for a period of 30 minutes to two hours. If the voltage remained constant over time, the procedure was repeated at a higher current. This procedure was continued until a point was reached when the voltage began to increase with time denoting the onset of polarization or fouling. The current density at that point was the PCD for that operating condition (salt concentration, pH, temperature, and linear velocity). The initial operating current density (8 Amps, 45 mA/$CM^2$) was chosen based on the PCD results.

The system was operated in a batch mode. Thus, the succinate broth was continually being demineralized. The electrodialysis process continued until the solution was demineralized to a desired degree. The following is a description of the operating procedure.

Charging

1. Drain the system (Note: the system should be filled with demineralized water at all times to keep membranes from drying out) and close the valves. (The volume of the lines and membrane stack has been previously determined).
2. Fill the diluting reservoir with the solution to be demineralized, 8-12 liters of sodium succinate broth.
3. Fill the concentrating reservoir with one liter of sodium succinate of a concentration similar to that of the diluting compartment. This ensures good initial conductivity and circulation rate in the concentrating compartment.
4. Fill the electrolyte reservoir with 4-6 liters of 1M sodium succinate or sodium sulfate.
5. Turn on pumps and open valves slowly. Allow liquid in all three lines to flow at a rate that the floats in the rotameter are barely lifted.
6. Open valves further allowing pressure in the lines to build up gradually such that the pressure differential between any two lines at no time exceeds 1 psig.
7. Continue opening valves until the desired flow rate is reached.
8. Turn on the circulating water bath to heat the diluting stream to desired temperature.

Membrane Equilibration

1. Turn on power supply to a reading of 0.2 amperes.
2. Continue running the system for 10 minutes.

Batch Operation

1. Set valves to desired flow rates.
2. Set power supply for desired current (the desired current was previously determined based on the permissible current density).
3. During the run, data collected included: current, voltage drop across total unit, voltage drop across eight cell pairs, volume levels in the diluting and concentrating compartments, pH of the diluting and electrolyte compartments, conductivity of the diluting compartment, and temperature of the diluting compartment.

4. The unit was operated at a constant current until the resistance started to increase thus increasing the voltage drop across the unit. At that time, a maximum voltage was set and the current was allowed to decrease until the end of the run.

5. Samples were taken at thirty minute intervals in addition to initial and final samples.

After the water-splitting electrodialysis, the acid product contains residual sodium and sulfate (and other anions). Ion exchangers are used to remove the sodium ions (Dowex 50Wx8) and sulfate ions (Rohm & Haas IRA-94). Two inch glass columns were used for ion exchange polishing of product streams from the water-splitting ED.

Operation of the two columns was done in the continuous flow mode. The ion exchange resins were charged, backwashed and conditioned as specified by the manufacturers. The bed volume (volume of resin under the above conditions) was determined at this time. In the adsorption step a flow rate of 0.01 bed volumes/minute was used. The succinic/acetic acid solution was approximately 1N. The sodium concentration was 0.2 to 0.3N. Bed volume for cation exchange was double the required based on the Dowex 50Wx8 capacity of 1.8 milliequivalents per ml.

Bed volume for the anion exchanger was double the required ion exchange capacity based on the sulfate content of the solution. IRA-94 exchange capacity was 1.3 milliequivalents per ml.

Regeneration of columns was achieved per manufacturers specifications.

Analytical Methods

Conductivity was measured using a portable conductivity meter (Cole Parmer model 1484-10).

Succinate and acetate concentrations reported are the anion concentration and were measured after appropriate dilution and acidification by an HPLC method using a 1 ft long HPx87 H+ column of BioRad (California, U.S.A.).

Total protein content was determined by Kjeldahl apparatus and reported as nitrogen x 6.25%.

Sulfate concentration was determined by gravimetric determination of barium sulfate precipitation. Sodium concentration was determined using an Orion SA 720 ion selective meter and a sodium electrode.

Definition of Terms

Current Density—current per unit area of available membrane through which current passes. The higher the applied current density, the lower cell area required to achieve a specific degree of ion transfer.

Current Efficiency—ratio of the number of equivalents of organic acid transferred to the number of Faradays of electricity passed through the membrane.

Flux—volume transferred through the available membrane area in a specific time.

EXAMPLES 1-5

Fermentation

*A. succiniciproducens* fermentations were conducted to obtain a high yield and productivity of succinate. Fermentations were conducted in 2 l New Brunswick Multigen Fermentor at various controlled pH values, with various $CO_2$ concentrations, with and without establishment of carbonate buffered conditions and using various monovalent cation alkalis.

The results of *A. succiniciproducens* fermentation at several different controlled pH values are summarized in Table 2. The pH was controlled at values ranging from 5.5 to 7.2. The organism did not grow or consume substrate at a pH of 5.5. The optimal pH range for high succinate yield is 5.8 to 6.6. The optimal pH for succinate productivity is 5.9 to 6.3. The maximum succinate yield is in the 87 to 90 weight percent based on dextrose consumed. At pH values higher than 6.6 succinate yield is low and lactate is produced. Under optimal pH (5.8-6.6) conditions the major byproduct, other than succinate, is acetate.

TABLE 2

*A. SUCCINICIPRODUCENS* FERMENTATION PRODUCTS AT VARIOUS PH VALUES

|  | Ex. 1 pH 5.9 | Ex. 2 pH 6.1 | Ex. 3 pH 6.4 | Ex. 4 pH 6.8 | Ex. 5 pH 7.2 |
|---|---|---|---|---|---|
| Dextrose (Initial), g/l | 58.0 | 49.8 | 47.5 | 57.3 | 59.3 |
| Dextrose (Final), g/l | 1.9 | 0.0 | 0.5 | 1.6 | 1.8 |
| Fermentation Time, hrs | 24 | 22.5 | 38 | 29 | 41 |
| Products |  |  |  |  |  |
| Succinate, g | 50.3 | 43.5 | 41.2 | 20.2 | 14.7 |
| Acetate, g | 13.6 | 11.3 | 11.5 | 5.4 | 4.3 |
| Formate, g | 1.3 | 0.6 | 0.5 | 2.1 | 1.7 |
| Lactate, g | 0 | 0 | 0.0 | 20.6 | 39.6 |
| Succinate Yield, wt (%) | 89.7 | 87.3 | 87.8 | 36.3 | 25.6 |
| Lactate Yield, wt (%) | 0 | 0 | 0 | 37.0 | 68.9 |

Note: At pH 5.5 - only small amount of glucose was consumed.

EXAMPLES 6-8

Several different carbon dioxide concentrations in the sparged gas were used to determine how the fermentation was affected by carbon dioxide partial pressure. The results are summarized in Table 3. At low $CO_2$ partial pressure the succinate yield is low and the fermentation is slow and does not go to completion. Thus, a $CO_2$ partial pressure of greater than 0.1 atmospheric is required to produce succinate with high yield and rates.

TABLE 3

EFFECT OF $CO_2$ PARTIAL PRESSURE ON *A. SUCCINICIPRODUCENS* FERMENTATION

|  | Ex. 6 | Ex. 7 | Ex. 8 |
|---|---|---|---|
| $CO_2$ Partial Pressure (atm)+ | 0%* | 0.1% | 1.0% |
| Dextrose (Initial), g | 40.0 | 49.4 | 47.5 |
| Dextrose (Final), g | 17.5 | 32.9 | 0.6 |
| Fermentation Time, hrs | 40 | 43 | 38 |
| Succinate Productivity, g/l/hr | 0.01 | .27 | 1.1 |
| Products, g |  |  |  |
| Succinate | 0.6 | 11.6 | 41.2 |
| Acetate | 0.8 | 4.4 | 11.5 |
| Formate | 1.5 |  | 0.5 |
| Lactate | 13.5 |  | 0.0 |
| Ethanol | 1.2 | 0.4 | 0.0 |
| Succinate Yield, wt (%) | 2.6 | 70.3 | 87.8 |
| Lactate Yield, wt (%) | 60 | 0 | 0 |
| pH | 6.2 | 6.2 | 6.2 |

+Total gas rate 10 cm$^3$/min

EXAMPLES 9

Figure 3:
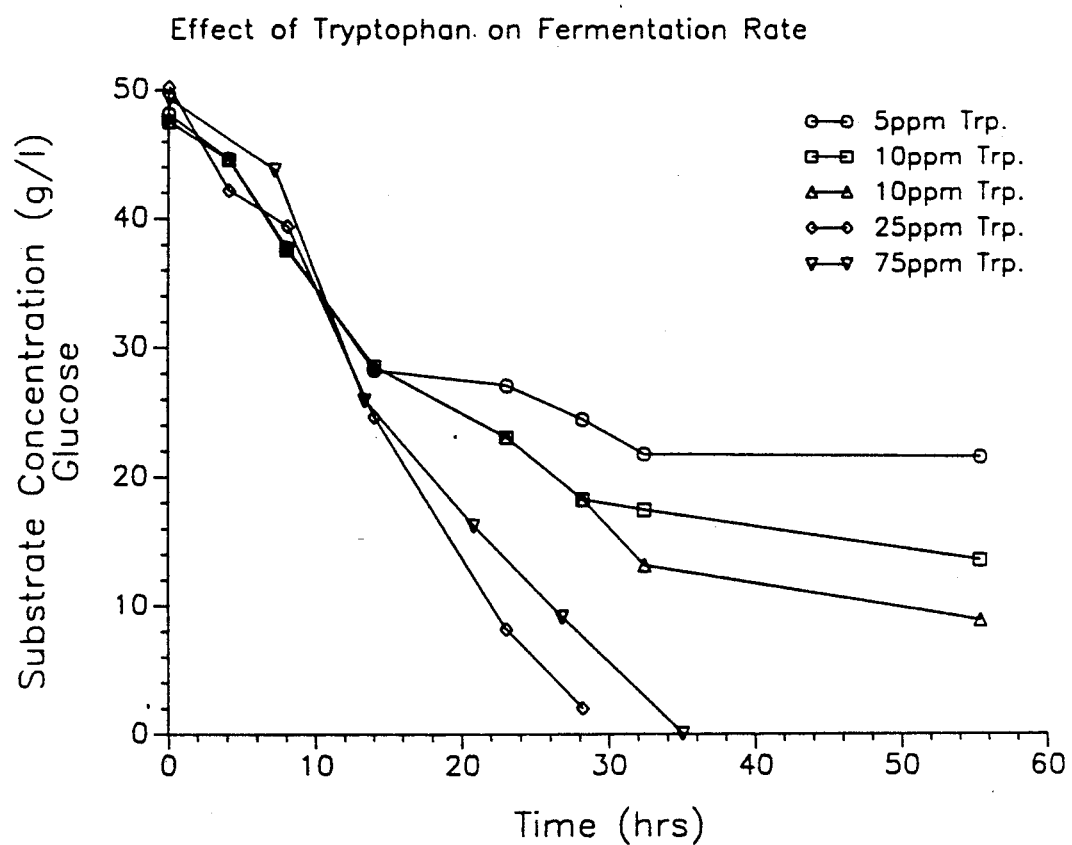

The effect of various concentrations of tryptophan is shown in the graph of FIG. 3. From this graph it can be seen that about 25 ppm tryptophan is the optimum level required for consumption of a high level of dextrose substrate. The use of lesser amounts of tryptophan, such as 10 ppm, is advantageous but they do not allow as complete a utilization of high levels of substrate.

EXAMPLES 10

Bases for neutralization are not restricted to the sodium cation only. Table 4 shows the results of using ammonium hydroxide as the neutralizing agent. The fermentation yield was 88 percent.

TABLE 4

*A. SUCCINICIPRODUCENS* FERMENTATION NEUTRALIZED WITH AMMONIUM HYDROXIDE

|  | Ex. 10 |
| --- | --- |
| Dextrose (Initial), g | 49.3 |
| Dextrose (Final), g | 2.5 |
| Fermentation Time, hr | 36 |
| Productivity, g/l/hr | 1.1 |
| Products |  |
| Succinate, g | 41.1 |
| Acetate, g | 10.7 |
| Lactate, g | — |
| Formate, g | 0.8 |
| Succinate Yield, % | 88 |
| Lactate Yield, % | 0 |
| pH | 6.0 |

The results from these experiments show that succinate fermentation with high yield and productivity occurs under certain carefully controlled conditions of fermentation pH, $CO_2$ partial pressures, nutrients and alkali addition.

EXAMPLE 11

The electrodialysis recovery process requires larger volumes of broth than 2 liter test fermentations. For this reason and to test the fermentation on a larger scale 80 liter fermentations were conducted.

Procedures and materials used in these fermentations have been previously described. Cysteine-HCl was used instead of cysteine sulfide for initial reduction of the media. The $CO_2$ was delivered under 5 psig pressure resulting in a succinate yield of nearly 90 percent, showing that higher $CO_2$ pressures lead to higher succinate yield. The results are summarized in Table 5.

TABLE 5

SCALE UP OF *A. SUCCINICIPRODUCENS* FERMENTATION FOR ELECTRODIALYSIS RECOVERY

|  | Ex. 11 |
| --- | --- |
| Dextrose (Initial), g | 1892 |
| Dextrose (Final), g | 0 |
| Fermentation Volume, l | 55 |
| Fermentation Time, hr | 28 |
| Productivity, g/l/hr | 1.1 |
| Products, g |  |
| Succinate | 1696.2 |
| Acetate | 462 |
| Lactate | — |
| Formate | 46 |
| Succinate Yield, wt. % | 89.7 |
| pH | 6.2 |

EXAMPLES 12-13

After consumption of all substrate 10 liters of the whole broth was immediately used for electrodialysis recovery of the succinate salt. The remainder of the broth was clarified using an Amicon DC-30 ultrafiltration hollow fiber membrane with a 0.2 micron pore size cut off value. This succinate salt containing broth, with cells removed, was used in comparative tests for electrodialysis recovery and purification.

The whole cell broth and clarified broth generated was processed using the conventional electrodialysis membrane stack. The performance of the separation was the same whether whole cell or clarified broth was used. The broth concentration in the dilute compartment initially was in the 20-25 g/l range. The final concentrate contained 90-95 g/l succinate. The initial acetate concentration in the dilute compartment was approximately 6.0 g/l. The final acetate concentration in the concentrate was approximately 13 g/l.

The ratio of succinate to acetate in the broth compartment is higher initially than it is at the end of the recovery process. The succinate to acetate (S/A) weight ratio in the broth compartment initially was 3.7. After 120 minutes the ratio was 2.4. Close to 80% of the succinate was recovered in each batch run. The acetate recovery was only 60% in each run.

A material balance on the succinate and acetate transported from the broth to the product concentrate shows that the succinate is preferentially transported across the preferred membranes under these operating conditions. This is a very important and unexpected discovery as it allows the preferential recovery of the desirable succinate from the broth, enriching its concentration in the product and leaving the undesirable acetate in the depleted broth.

The current efficiency for both the whole cell and clarified broth was approximately 80% based on the total organic acids transported. The results are summarized in Table 6.

TABLE 6

COMPARISON OF SUCCINIC ACID RECOVERY BY ELECTRODIALYSIS FROM WHOLE CELL BROTH AND CLARIFIED BROTH

|  | Ex. 12 Whole Cell Broth | Ex. 13 Clarified Broth |
| --- | --- | --- |
| Broth: |  |  |
| Initial Succinate Conc., g/l | 22.4 | 23.5 |
| Final Succinate Conc., g/l | 6.1 | 5.6 |
| Initial Acetate Conc., g/l | 5.9 | 6.3 |
| Final Acetate Conc., g/l | 2.5 | 2.8 |
| Concentrate |  |  |
| Initial Succinate Conc., g/l | 55.2 | 51.7 |
| Final Succinate Conc., g/l | 93.8 | 92.4 |
| Initial Acetate Conc., g/l | 0.0 | 0.0 |
| Final Acetate Conc., g/l | 12.8 | 13.2 |
| Succinate Removal, % | 76.1 | 79.0 |
| Acetate Removal, % | 59.2 | 61.0 |
| Length of Run, Minutes | 120 | 120 |
| Temperature, °C. | 50 | 50 |
| Current Efficiency, % | 80.2 | 81.1 |
| Initial Current Density, Mamp/$cm^2$ | 45 | 45 |
| Water Flux, gal/Hr $Ft^2$ | 0.94 | 0.89 |
| Average Water Transfer, ml/Fa | 287 | 276 |
| Protein Retained, % | 87.3 | 90.5 |
| Electricity Requirement, kwhr/lb |  |  |
| Succinic Acid Basis | .215 | .206 |
| All Organic Acids Basis | .175 | .169 |

The protein in the dilute feed broth and the concentrate were measured using the Kjeldahl total nitrogen method. Based on the total Kjeldahl nitrogen value 85 to 90 percent of all nitrogen containing compounds were retained in the dilute stream. Table 7 summarizes nitrogenous impurity (protein) rejection by the ED membranes.

TABLE 7

PROTEIN AND AMINO ACIDS TRANSPORT

| | Ex. 13 Clarified Broth | | Ex. 12 Whole Cell Broth | |
|---|---|---|---|---|
| | Feed Broth | Product (Concentrate) | Feed Broth | Product (Concentrate) |
| Volume (l) | 11.8 | 3.0 | 32.9 | 7.0 |
| Kjeldahl Protein (g/l) | 3.8 | 1.9 | 2.7 | 1.2 |
| Total Protein (g) | 44.8 | 5.7 | 88.8 | 8.4 |
| Protein Rejection (%) | | 87.3 | | 90.5 |

EXAMPLES 14

An electrodialysis run was made on clarified broth at a current density above the permissible current density (PCD). The results of conducting electrodialysis recovery at a current density above the PCD are summarized in Table 8.

TABLE 8

RESULTS OF SODIUM SUCCINATE RECOVERY WHEN ELECTRODIALYSIS EQUIPMENT OPERATED ABOVE THE PERMISSIBLE CURRENT DENSITY

| | Ex. 14 |
|---|---|
| Broth: | |
| Initial Succinate Conc., g/l | 23.3 |
| Final Succinate Conc., g/l | 5.4 |
| Initial Acetate Conc., g/l | 6.1 |
| Final Acetate Conc., g/l | 2.5 |
| Concentrate: | |
| Initial Succinate Conc., g/l | 23.1 |
| Final Succinate Conc., g/l | *80.3 |
| Initial Acetate Conc., g/l | 3.3 |
| Final Acetate Conc., g/l | 16.5 |
| Succinate Removal, % | 79.6 |
| Length of Run, Minutes | 105 |
| Temperature, °C. | 50 |
| Current Efficiency, % | 78.2 |
| Initial Current Density, Mamp/cm$^2$ | 67.4 |
| Average Water transfer, ml/Fa | 266 |
| Electricity Requirement, kwhr/lb | |
| Succinic Acid Basis | .37 |
| All Organic Acids Basis | .30 |

The major result is a greatly increased electricity requirement. The PCD was exceeded by less than 50%, but the power requirement nearly doubled.

These results show that by proper selection of the fermentation organism, media, electrodialysis membranes and careful control of the operating conditions for the electrodialysis process a very efficient and useful recovery and purification step is discovered. In this step, succinate salt can be preferentially recovered from whole or clarified broth and a purified succinate salt containing approximately 0.8% nitrogenous impurities, such as protein, on a dry basis is produced.

EXAMPLES 15-16

The concentrated and purified succinate salt stream from conventional electrodialysis is further processed using a bipolar, water-splitting membrane stack (Aquatech-Allied Signal). Results obtained using the bipolar membrane stack described previously are shown in Table 9. Example 15 was done on material coming directly from conventional ED. Example 16 was done on a stream from conventional ED that was concentrated by evaporation prior to processing by the bipolar membrane stack.

TABLE 9

SUMMARY OF SUCCINIC ACID RECOVERY FROM SODIUM SUCCINATE USING WATER-SPLITTING ELECTRODIALYSIS

| | Ex. 15 | Ex. 16 |
|---|---|---|
| Sodium Removal, % | 78.9 | 81.2 |
| Sodium Conc. after ED, g/l | 6.4 | 4.8 |
| Salt Stream | | |
| Initial Succinate Conc., g/l | 78 | 126 |
| Final Succinate Conc., g/l | 91 | 152 |
| Initial Acetate Conc., g/l | 13 | 29 |
| Final Acetate Conc., g/l | 15 | 36 |
| Length of Run, Min | 110 | 100 |
| Temperature, °C. | 45 | 45 |
| Current Efficiency, % | 78.9 | 76.2 |
| Initial Current Density, Mamp/cm$^2$ | 127 | 127 |
| Electricity Requirement, kwhr/lb | | |
| Succinic Acid Basis | 0.57 | 0.51 |
| Total Organic Acid Basis | 0.48 | 0.42 |

The major differences between using the lower and higher initial succinate concentrations is shown by the electricity requirements and residual sodium concentrations. Higher initial succinate salt concentration results in a lower power consumption and a lower residual sodium cation concentration. Thus, concentrating the product from conventional ED by simple evaporation is desirable to reduce power consumption and costs associated with the sodium cation removal. This is especially the case if succinic acid product concentration needs to be higher than is provided by the conventional ED recovery.

Preferential transport of dicarboxylic acids compared to monocarboxylic acids is likely to occur in the water-splitting ED system if a 3 compartment cell configuration is used. A three compartment operation was not used because power consumption and membrane costs would be much higher. If a higher ratio of succinate to acetate was desired, three compartment water-splitting ED may be used.

Total power consumption per pound of succinic acid by the two ED processes is about 0.67 kilowatt hour. Table 10 shows that the organic acid purity (dry basis) increases from 64.7% after fermentation to 96.2% after water-splitting electrodialysis. The dry basis composition of the product stream is shown at each step of the recovery process. Nitrogenous impurities (protein) content is reduced from 9.7 to 0.6% during the two-stage electrodialysis recovery process.

EXAMPLE 17

The succinic acid stream after water-splitting ED contains some residual sodium ions, amino acids and sulfate ions. A polish ion exchange system was developed to first remove the sodium cation, then to remove the sulfate anion. Along with the removal of sodium and sulfate ions some of the amino acids were removed.

A strongly acidic cation exchanger (Dowex 50W×8) was used in the acid form to remove sodium from the succinic acid stream. A weakly basic anion exchange resin (Rohm and Haas IRA-94) in the free base form was then used to preferentially remove the sulfate from the succinic acid stream. Sodium and sulfate concentrations are reduced below 5 ppm. Results obtained using the ion exchangers are summarized in Table 10. The ion exchange resins, especially the cation exchange resin, help to reduce the amino acids in the product. The purity of the succinic/acetic acid product is 99.5% dry basis after the ion exchange processing and contained less then 0.5% nitrogenous impurities. Thus, by the careful selection of processing steps, a product that contains less then 1% of nitrogenous impurities and less than 10 ppm sulfate and sodium and other cation ions can be produced by the fermentation and purification process of the present invention.

TABLE 10
PROCESS STREAM COMPOSITIONS
(Weight % Composition, Dry Basis)

|  | Fermentor Product | After ED* | After Water-Splitting ED | After Cation Exchange | After Anion Exchange |
|---|---|---|---|---|---|
| Succinate | 51.5 | 63.0 | 77.6 | 82.7 | 79.6 |
| Acetate | 13.2 | 8.8 | 18.6 | 16.1 | 19.9 |
| Nitrogenous Impurity (Protein) | 9.7 | .8 | .6 | .5 | .5 |
| Sodium | 25.6 | 27.3 | 2.8 | — | — |
| Sulfate (ppm) | 0.1 | 0.6 | 0.4 | 0.4 | — |

*Data from batch recovery; succinate/acetate ratio high because concentrate initially contains only succinate.

It will be apparent to those skilled in the art that the combination of the special strain of *A. succiniciproducens* and the use of fabric reinforced, microheterogeneous interpolymer membranes (Asahi Glass AMV and CMR) permits simultaneous electrodialysis and cell recycle from whole broth to be achieved without loss of efficiency either in the fermentor or the electrodialysis separator. The mature cells remain viable and are recycled to the fermentor where fermentation continues with addition of carbohydrates and nutrients, and the purified and concentrated succinate from the electrodialyzer can be used to feed the water-splitting electrodialysis system, such as the "AQUATECH" system, where the succinate salt is converted to succinic acid and the corresponding base. The base obtained can be recycled to the fermentor for neutralization, and purified concentrated succinic acid further purified with ion exchangers for use as a specialty chemical or a commodity chemical intermediate.

It is extremely important that the succinate salt stream from the fermentation be first treated by conventional electrodialysis to recover the succinate salt and remove the nitrogenous impurities; that it next be treated with watersplitting electrodialysis to convert the succinate salt to succinic acid and that the resulting succinic acid stream be treated first with a strongly acidic ion exchanger and then a weakly basic ion exchanger to obtain the desired product. Unless this order of steps is followed a satisfactory product cannot be obtained.

It also will be apparent to those skilled in the art that for a fermentation process to economically produce succinic acid and its derivatives economically enough for use as specialty and commodity chemicals, it is necessary that the process use low cost nutrients, produce high product concentration at a high productivity and that the process be integrated with an economical purification process. The novel process of the present invention meets those requirements.

It is intended that the scope of the present invention not be limited except by the claims.

REFERENCES

1. Howlett, et al., *Applied Environ. Microbiol.*, 32, 274-283 (1976).
2. Caldwell, et al., *J. Bacteriol.*, 98, 668-676 (1969). Hamlin, et al., *J. Bacteriol.*, 72, 548-554 (1956).
3. 
4. Anderson and Ordal, *J. Bacteriol.*, 81, 139 (1961).
5. Caspari, et al., *Arch Microbiol.*, 135, 16-24 (1983).
6. Prigent, Y., "Lactic acid production by fermenting whey--using e.g. Lactobacillus; ultrafiltration and recovery of the lactic acid from the permeate by electrodialysis", French Patent Appl. FR 2555-200, 83 18631, Nov., 1983.
7. Hongo, M., Nomura, Y. and M. Iwahara, "Novel Method of Lactic Acid Production by Electrodialysis Fermentation", Appl. Environ. Microbiol. 52, 2, 314-319, Aug., 1986.
8. Nomura, Y., Iwahara, M. and M. Hongo, "Lactic Acid Production by Electrodialysis Fermentation Using Immobilized Growing Cells". Biotechnol. Bioeng. 30, 788-793, Oct., 1987.
9. K. M. Mani, F. P. Chlanda and C. H. Byszewski, "AQUATECH TM Membrane Technology for Recovery for Acid/Base Values from Salt Streams," Desalination, 68, 149-166, (1988).
10. Davis, T.A., "Recent Developments in Electrodialysis," paper presented at the Sixth Annual Membrane Technology/Planning Conference, November 1-3, 1988, Cambridge, Mass.
11. Mani, K. and W. L. Johnson, "Bipolar Membranes: Technology Review/Application," paper presented at the Sixth Annual Membrane Technology/Planning Conference, Nov. 1-3, 1988, Cambridge, Mass.
12. Chlanda, F.P. and M. J. Lan, "Bipolar Membranes and Methods of Making Same," U.S. Pat. No. 4,766,161 (1988).

We claim:
1. A process for producing succinic acid of high purity which comprises:
(a) growing an anaerobic organism which has all the identifying characteristics of *Anaerobiospirillum succiniciproducens* ATCC No. 53488 under anaerobic conditions in a fermentor on a medium containing at least 20g/l of assimilable carbohydrate and other required nutrients in the presence of dissolved carbon dioxide in equilibrium with a partial pressure of at least 0.1 atmosphere of carbon dioxide while maintaining the pH within the range of 5.8 to 6.4 until a succinate salt in a yield of at least 50 weight percent based on consumed carbohydrate is formed in the broth;
(b) subjecting the broth containing the succinate salt first to desalting electrodialysis to preferentially recover and concentrate the succinate salt into an aqueous stream and to remove nitrogenous impurities; and
(c) subjecting the aqueous stream containing the concentrated succinate salt from the desalting electrodialysis to water-splitting electrodialysis to convert the succinate salt to a base and a succinic acid stream.

2. A process of claim 1 which further includes;

(d) treating the succinic acid stream first with a strongly acidic ion exchanger in the acid form to remove sodium or other cations for the stream without removing the succinic acid; and (e) then treating the thus treated succinic acid stream with a weakly basic ion exchanger int eh free base form to remove sulfate and other strongly anionic impurities from the stream without removing the succinic acid to obtain a succinic acid stream containing less than 1% nitrogenous impurities.

3. A process of claim 1 in which any viable cells in the broth from which succinate salt has been removed are recycled to the fermentor.

4. A process of claim 1 in which the base obtained in step (c) is returned to the fermentor.

* * * * *